United States Patent [19]

Gerstenberg et al.

[11] Patent Number: 5,447,912
[45] Date of Patent: *Sep. 5, 1995

[54] ERECTION-INDUCING METHODS AND COMPOSITIONS

[75] Inventors: Thomas Gerstenberg; Bent Ottesen, both of Frederiksberg; Jan Fahrenkrug, Hellerup; Nicholas J. Coppard, Hojbjerg, all of Denmark

[73] Assignee: Senetek, PLC, Maryland Heights, Mo.

[ * ] Notice: The portion of the term of this patent subsequent to Aug. 17, 2010 has been disclaimed.

[21] Appl. No.: 107,266

[22] Filed: Aug. 16, 1993

Related U.S. Application Data

[63] Continuation-in-part of Ser. No. 408,754, Sep. 18, 1989, Pat. No. 5,236,904.

[51] Int. Cl.$^6$ .................... A61K 38/00; C07K 5/00; C07K 7/00; C07K 17/00
[52] U.S. Cl. .................................... 514/12; 530/324
[58] Field of Search ................ 514/12; 530/324; 435/810

[56] References Cited

U.S. PATENT DOCUMENTS

| | | | |
|---|---|---|---|
| 3,898,329 | 8/1975 | Said et al. | 424/177 |
| 4,605,641 | 8/1986 | Bolin et al. | 514/12 |
| 4,757,133 | 6/1988 | Ito et al. | 530/324 |
| 4,853,371 | 8/1989 | Coy et al. | 514/12 |
| 4,885,164 | 12/1989 | Thurow | 424/85.4 |
| 4,935,491 | 6/1990 | Folkers et al. | 530/313 |
| 4,935,492 | 6/1990 | Lewicki et al. | 530/324 |
| 4,939,224 | 3/1990 | Musso et al. | 530/324 |
| 5,147,855 | 9/1992 | Gozes et al. | 514/12 |
| 5,217,953 | 6/1993 | Gozes et al. | 514/12 |
| 5,236,904 | 8/1993 | Gerstenberg et al. | 514/12 |

FOREIGN PATENT DOCUMENTS

| | | |
|---|---|---|
| 0184309A2 | 11/1986 | European Pat. Off. . |
| 0225639A2 | 6/1987 | European Pat. Off. . |
| 0297068A2 | 12/1988 | European Pat. Off. . |
| 0354992 | 2/1990 | European Pat. Off. . |
| 0357591 | 3/1990 | European Pat. Off. . |
| 0540969A2 | 12/1993 | European Pat. Off. . |
| 3637157 | 5/1987 | Germany . |
| 9104039 | 4/1991 | WIPO . |

OTHER PUBLICATIONS

Robberecht et al., "Interaction of vasoactive intestinal peptide (VIP) and N-terminally modified VIP analogs with rat pancreatic, hepatic and pituitary membranes", Eur. J. Biochem., 159 (1986) pp. 45–49.

Fournier et al., "Synthesis, Conformational Studies and Biological Activities of VIP and Related Fragments", Peptides, vol. 5 (1984), pp. 169–177.

(List continued on next page.)

Primary Examiner—Jill Warden
Assistant Examiner—A. M. Davenport
Attorney, Agent, or Firm—Fitch, Even, Tabin & Flannery

[57] ABSTRACT

Methods and compositions for inducing penile erections, sufficient for vaginal penetration, in a human male suffering from impotence are provided. Kits containing the compositions in containers for single dosage administration are provided.

Compositions for treating impotence that is of psychogenic or neurogenic origin contain a neuropeptide, vasoactive intestinal peptide and/or peptide N-terminal histidine C-terminal methioneamide and are formulated in a pharmaceutically acceptable carrier that has a pH of about 2 to about 4.5, preferably between about 2 and about 3.5, and most preferably about 3. Compositions for treating impotence of almost origin, including severe atherosclerosis, contain a neuropeptide, vasoactive intestinal peptide and/or peptide N-terminal histidine C-terminal methioneamide, and an α-adrenergic blocker, such as phentolamine or prazosin.

In practicing the methods, the composition is administered by intracavernosal injection accompanied by or followed by sexual stimulation.

23 Claims, No Drawings

Couvineau et al., "Structural Requirements for VIP Interaction With Specific Receptors in Human and Rat Intestinal Membranes: Effect of Nine Partial Sequences", *Biochemical and Biophysical Research Communications*, vol. 121, No. 2, Jun. 15, 1984, pp. 493–498.

Gerdin et al., "Structural Requirements for Microvascular Permeability-Increasing Ability of Peptides" i Biochimica et al Biophysical Acta, 757 (1983) pp. 366–370.

Weihe et al., "Distribution of vasoactive intestinal polypeptide-like immunoreactivity in the mammalian heart interrelation with neurotensin-and substances P-like immunoreactive nerves", *Cell Tissue Research*, (1984) 236:pp. 527–540.

Tischler et al., "Prodcution of 'Ectopic' Vasoactive Intestinal Peptide-Like and Neurotensin-Like Immunoreactivity in Human Pheochromocytoma Cell Cultures", *The Journal of Neuroscience*, vol. 4, No. 5, pp. 1398–1404.

Endo et al., "Effects of Intraventricular Administration of Vasoactive Intestinal Peptide and Neurotensin heat Interrelation with neurotensin-and substances P-like immunoreactive nerves", *Cell Tissue* on Neurotensin on Salivary Seretion and Blood Pressure in the Rat *Endocrinol. Japan*, 1987, 34(6), pp. 927–935.

Schaaper et al. "Synthesis of Vasoactive Intestinal Peptide (VIP) via the Mixed Anhydride Method", *Peptides*, vol. 5, pp. 167–168.

Turner et al., "A Fragment of Vasoactive Intestinal Peptide, VIP(10-28), is an Antagonist of VIP in the Colon Carcinoma Cell Line, HT29", *Peptides*, vol. 7, (1986), pp. 849–854.

"Neoplasms", *The Merck Manual of Diagnosis and Therapy*, 11th Ed., (1966) pp. 1368–1371.

"Effects of Chronic Hyperprolactinemia on Sexual Arousal and Erectile Function in Male Rats", *Neuroendocrinology*, 42, (1986), pp. 368–375.

Ottesen, et al., "Vasoactive intestinal polypeptide (VIP) increases vaginal blood flow and inhibits uterine smooth muscle activity in women," *Euro. Journal of Clinical Investigation* 13:321–324 (1983).

Wagner, et al., "Intracavernosal injection of vascoactive intestinal polypeptide (VIP) does no induce erection in man per se," *World Journal Urol.*, 5:171–172 (1987).

Kiely, et al., "Penile response to intracavernosal vasoactive intestinal polypeptide alone and in combination with other vasoactive agents," *British Journal of Urology*, 64:191–194 (1989).

Brindley, "Cavernosal alpha-blockade: a new technique for investigating and treating erectile impotence," *British Journal Psychiat.*, 143:332–337 (1983).

Willis, et al., "Vasoactive intestinal polypeptide (VIP) as a putative neurotransmitter in penile erection," *Life Sciences*, 33:383–391 (1983).

Ottesen, et al., "Penile erection: possible role for vasoactive intestinal polypeptide as a neurotransmitter," *British Medical Journal*, 288:9–11 (1984).

Adaikan, et al., "Is vasoactive intestinal polypeptide the principal transmitter involved in human penile erection?" *The Journal of Urology*, 135:638–640 (1986).

Itoh, et al., "Human preprovasoactive intestinal polypeptide contains a novel PHI-27-like peptide, PHM-27," *Nature*, 304:547–549 (1983).

Weiner, "Drugs that inhibit adrenergic nerves and block adrenergic receptors", in Goodman and Gilman, eds., *The Pharmacological Basis of Therapeutics*, MacMillan Publishing Co., New York, New York, 6th Ed., Chapter 9:176–210 (1980).

Blum et al., "Effect of local alpha-adrenergic blockade on human penile erection," *J. Urol.* 134(3):479–481 (1985), Abstr. from *Dialog Info. Ser.* File 155 AN=5677264.

Gerstenberg, et al., "Intracavernous self-injection with vasoactive intestinal polypeptide and phentolamine in the management of erectile failure," *J. Urol.* 147:1277–1279 (1992).

Yianguo, et al., "Peptide histidine methionine (PHM) and the human male genitalia," *Neuropeptides* 6(2): 133–142 (1985).

Kirkeby, et al., "Effects of vasoactive intestinal peptide, peptide histidine methionine, and neuropeptide Y on intracavernous pressure in the rabbit," *Urology* 40(3):270–276 (1992).

Fahrenkrug, et al., "Vasoactive intestinal polypeptide and the reproductive system," *Ann. N.Y. Acad. Sci.* 527:393–404 (1988).

Polak and Bloom, "Localisation and measurement of VIP in the genitourinary system of man and animals," *Peptides* 5:225–230 (1984).

Bodner, et al., "Coding sequences for vasoactive intestinal peptide and PHM-27 peptide are located on two adjacent exons in the human genome," *P.N.A.S.* 82:3548–3551 (1985).

(List continued on next page.)

OTHER PUBLICATIONS

Willis et al., "Vasoactive intestinal polypeptide (VIP) as a possible neurotransmitter involved in penile erection," *Chem. Abs.* 96:4180p (1982).

Kirkeby et al., "Vasoactive intestinal polypeptide (VIP) and petide histidine methionine (PHM) in human penile corpus cavernosum tissue and circumflex veins: localization and in vitro effects," *Euro. J. Clinic. Invest.* 22:24–30 (1992).

Fahrenkrug and Pedersen, "Cosecretion of peptide histidine methionine (PHM) and vasoactive intestinal peptide (VIP) in patients with VIP-producing tumors," *Peptides* 7:717–721 (1986).

Palle et al., "Peptide histidine methionine and vasoactive intestinal peptide: Occurrence and relaxant effect in the human female reproductive tract," *Biol. Repro.* 41:1103–1111 (1989).

ERECTION-INDUCING METHODS AND COMPOSITIONS

RELATED APPLICATIONS

This application is a continuation-in-part of U.S. application Ser. No. 07/408,754, filed Sep. 18, 1989, and now U.S. Pat. No. 5,236,904 to Thomas Gerstenberg, Jan Fahrenkrug and Bent Ottesen, entitled "ERECTION-INDUCING METHODS AND COMPOSITIONS". The subject matter of U.S. application Ser. No. 07/408,754 is incorporated herein in its entirety.

The subject matter of this application is related to the subject matter of copending U.S. application Ser. Nos. 07/956,952, now pending 07/740,843, now U.S. Pat. No. 5,360, 410 and 07/641,752, now U.S. Pat. No. 5,354,287 to Wacks. The subject matter of each of these applications is herein incorporated in its entirety.

1. Field of the Invention

The present invention concerns methods and compositions for inducing penile erections in human males suffering from impotence.

2. Background

Impotence or erectile insufficiency is a widespread disorder that is thought to affect about twelve percent of adult men under age forty-five, about twenty percent of men at age sixty, and about fifty-five percent of men at age seventy-five. A number of causes of erectile insufficiency, in addition to anatomical deficiencies of the penis or scrotum that preclude an erection sufficient for vaginal penetration, have been identified. These causes are psychological and physical in origin and in any individual suffering from impotence there may be more than one cause of erectile dysfunction. Erectile dysfunction can be psychological, resulting, for example, from anxiety or depression, with no apparent somatic or organic impairment. Such erectile dysfunction, which is referred to as "psychogenic", is responsible for about fifteen to twenty percent of cases of impotence. In other cases, the erectile dysfunction is associated with atherosclerosis of the arteries supplying blood to the penis; such dysfunction is referred to as "arteriogenic" or "atherosclerotic." About forty to sixty percent of cases of impotence are arteriogenic in origin. In still other cases, there is leakage from veins in the penis such that sufficient pressure for an erection can be neither obtained nor maintained, This dysfunction is referred to as "venous leakage," or "abnormal drainage". This condition is often exacerbated by the presence of some arteriogenic dysfunction whereby the supply of blood to the penis is impaired. In still other cases, the dysfunction is associated with a neuropathy, such as nerve damage arising from, for example, surgery or a pelvic injury, in the nervous system affecting the penis. Such a dysfunction is referred to as "neurogenic" and about ten to fifteen percent of cases of impotence are neurogenic in origin.

There is also a high incidence of erectile insufficiency among diabetics, particularly those with insulin-dependent diabetes mellitus. Erectile dysfunction in diabetics is often classified as "diabetogenic," although the underlying dysfunction is usually neurogenic associated with neuropathy, but may be arteriogenic or neurogenic and arteriogenic. About half of diabetic males suffer from erectile insufficiency, and about half of the cases of neurogenic impotence are in diabetics.

Erectile insufficiency is sometimes a side effect of certain drugs, such as beta-blockers that are administered to reduce blood pressure in persons suffering from hypertension, or drugs administered to treat depression or anxiety. Excessive alcohol consumption has also been linked to erectile insufficiency. These forms of erectile insufficiency may be regarded as a subset of neurogenic or psychogenic insufficiency.

A number of methods to treat impotence are available. These treatments include pharmacological treatments, surgery and, in cases of psychogenic dysfunction, psychological counseling is sometimes effective. Psychogenic impotence often can be cured by counseling coupled with a demonstration to the patient that he is capable of having a full erection by inducing such an erection one of a few times in the patients. Insufficiency due to excessive alcohol consumption is sometimes cured by reducing or elimination such consumption.

In the rare cases, where the insufficiency is untreatable because of venous leakage, surgery can usually be employed to repair the venous lesion and thereby either cure the insufficiency or, if there remains an erectile insufficiency after repair of the venous lesion, render the insufficiency amenable to treatment by pharmacological methods. Also, penile implants, which provide a mechanic means to produce an erection sufficient for vaginal penetration, are widely used to treat impotence. In recent years, implants have been employed, especially in cases where pharmacological intervention is ineffective, which are usually cases of severe atherogenic impotence. Treatment of impotence with penile implants, however, entails serious disadvantages. Such treatment requires surgery and necessitates total destruction of the erectile tissues of the penis, forever precluding normal erection.

Pharmacological methods of treatment are also available. Such methods, however, have not proven to be highly satisfactory or without potentially severe side-effects. Papaverine is now widely used to treat impotence, although papaverine is ineffective in overcoming impotence due, at least in part, to severe atherosclerosis. Papaverine is effective in cases where the dysfunction is psychogenic or neurogenic and severe atherosclerosis is not involved. Injection of papaverine, a smooth muscle relaxant, or phenoxybenzamine, a non-specific blocker and hypotensive, into a corpus cavernosum has been found to cause an erection sufficient for vaginal penetration. Also, in cases where severe atherosclerosis is not a cause of the dysfunction, intracavernosal injection of phentolamine, an alpha-adrenergic blocker, causes an erection sufficient for vaginal penetration. The resulting erection is one of significantly shorter duration than that induced by intracavernosal injection of papaverine or phenoxybenzamine and is of such short duration that satisfactory sexual relations are difficult or impossible.

Treatment of impotence with papaverine or phenoxybenzamine often results in priapism, a locking-up of an erection for a long period of time, typically a few hours and sometimes longer than twenty-four hours. Priapism is a serious, deleterious side effect of treatment of erectile insufficiency with these drugs. Beyond the embarrassment that may be caused for some men, priapism is usually painful, irreversibly damages erectile tissue, and, to be relieved, requires bleeding or pharmacological intervention, such as injection of a sympathomimetic drug, such as adrenaline. Even if priapism does not occur with use of papaverine, such use is associated with a painful, burning sensation in the first two or so minutes after the injection and there are indications that repeated use of papaverine causes undesirable, extensive intracavernous fibrosis. Further, as indicated above, impotence arising from severe atherosclerosis is not susceptible to treatment with papaverine, phenoxybenzamine, phentolamine or papaverine together with phentolamine. In any case, phenoxybenzamine is not suitable for use in treating impotence because it is a carcinogen.

The neuropeptide, human vasoactive intestinal peptide (hereinafter referred to as "VIP"), is thought to be associated with erections in normal males (i.e., males not suffering from erectile insufficiency). Injection of up to 20 μm of VIP (at 20 μm/ml of diluent), however, into a corpus cavernosum of a normal male, without subjecting the male to sexual stimulation, causes only slight swelling (slight tumescence) of the penis but not an erection. When coupled with visual sexual stimulation, sexual stimulation by vibration, or both types of stimulation, as little as 1 μm of the neuropeptide (at 1 μm/ml of diluent)injected into a corpus cavernosum of a normal male facilitates full erection (see, Wagner et al. (1987) *World J. Urol.* 5:171–172). Doses of VIP that, on one hand, are adequate (when coupled with sexual stimulation) to induce erections in males suffering from impotence but that, on the other hand, minimize or avoid systemic side effects due to administration of VIP (such as flushing of the skin and hypotension) were not identified. VIP alone or coupled with sexual stimulation does not induce erections in males whose impotence is due to severe atherosclerosis.

Thus, although impotence is a ubiquitous problem, there are few satisfactory methods available for treating this disorder. Therefore, it is an object herein to provide methods and compositions for treating impotence.

SUMMARY OF THE INVENTION

Compositions for treating impotence of any origin, other than causes that preclude an erection or that cannot be treated pharmacologically, are provided. The compositions contain an amount of VIP and/or peptide N-terminal histidine C-terminal methionineamide (hereinafter referred to as PHM ) and an α-adrenergic blocker that, when coupled with sexual stimulation, induce an erection, sufficient for vaginal penetration, in a male suffering from severe atherosclerosis. These compositions are particularly suitable for treating impotence caused by severe atherosclerosis but may be used to treat impotence of neurogenic and psychogenic origin. Compositions that are suitable for treating impotence that is substantially only psychogenic or neurogenic in origin are also provided. These compositions contain an amount of VIP and/or PHM that, when coupled with sexual stimulation, is effective for inducing an erection in a male suffering from impotence that is psychogenic or neurogenic in origin. In all cases the compositions are formulated in a carrier that is suitable for intracavernosal injection and that are buffered at a pH between about 2 and about 4.5, preferably about 2 and about 3.5, and most preferably about 3.

Methods of treatment of impotence and compositions for effecting such treatment are also provided herein. The methods for treating impotence are suitable for treating impotence of any origin, including, severe atherosclerosis, except for impotence arising from anatomical conditions that preclude an erection. The impotence is treated effectively by intracavernosal injections of VIP and/or PHM in combination with an alpha-adrenergic blocker, such as phentolamine or prazosin, followed by or coupled with sexual stimulation.

Methods of treatment of impotence that is of psychogenic or neurogenic origin are also provided. In practicing these methods, the neuropeptide, PHM and/or VIP, is injected intracavernosally, followed by or coupled with sexual stimulation.

Induction of an erection with VIP or PHM in accordance with the methods herein advantageously does not entail priapism or the burning pain associated with such induction with papaverine. Further, intracavernosal injection of VIP and/or PHM in combination with an alpha-adrenergic blocker provides an effective, nonsurgical method for inducing erections in males suffering from impotence due to severe atherosclerosis. These methods advantageously avoid the surgery necessary for, and the tissue destruction caused by, penile implants, the only effective means know heretofore for treating severely atherosclerotic impotence.

Kits containing the compositions in ampules or other suitable packaging means formulated for single dosage administration are provided. In preferred embodiments, the kits also contain an injector, preferably the injector described in copending U.S. application Ser. Nos. 07/956,952 and 07/641,752 to Wacks.

DETAILED DESCRIPTION OF PREFERRED EMBODIMENTS

Definitions

Unless defined otherwise, all technical and scientific terms used herein have the same meaning as is commonly understood by one of skill in the art to which this invention belongs. All patents and publications referred to herein are incorporated by reference.

As used herein, impotence refers to erectile insufficiency such that vaginal penetration is not possible.

As used herein, impotence that is "substantially only neurogenic or psychogenic" origin is substantially only neurogenic, psychogenic or neurogenic and psychogenic in origin. This, in turn, means impotence that is not due to an anatomical deficiency that precludes an erection sufficient for vaginal penetration (e.g., lack of a penis or a substantial portion thereof), and that is not untreatable because of venous leakage or and is not caused by severe or untreatable atherosclerosis.

As used herein, impotence, "of which severe atherosclerosis is a cause", is meant impotence that is caused, at least in part, by "severe" atherosclerosis but is not associated with an anatomical deficiency, which would preclude an erection sufficient for vaginal penetration, is not untreatable because of venous leakage, and, although it can be contributed to by neurological or psychological factors, is not "substantially only neurogenic or psychogenic" in origin as used herein.

As used herein, "severe" atherosclerosis is differentiated from "untreatable" atherosclerosis. In untreatable atherosclerosis, the arteries of the penis are so severely blocked that pharmacological treatments could not be effective in inducing an erection sufficient for vaginal penetration.

As used herein, impotence that is due to "untreatable" venous leakage means impotence that, due to venous leakage, cannot be effectively treated pharmacologically, although it might be correctable by repairing the venous leakage surgically.

As used herein, "intracavernosal" injection is injection into either corpus cavernosum of the penis. Such injection is carried out by any conventional injection means (e.g., employing an hypodermic syringe and needle or a similar device such as the NovolinPen ™ sold by Squibb-Novo, Inc., Princeton, N.J., USA or that of copending U.S. application Ser. No. 07/740,843) and is preferably carried out using the injection device described in copending U.S. application Ser. Nos. 07/956,952 and 07/641,752 to Wacks, by the male injecting himself or by another person (such as a partner during sexual relations or a physician prior to sexual relations) injecting the male whose erection is to be induced.

As used herein, the term "consisting essentially of" in connection with a substance that is part of a composition means that the substance is the only one in the composition that is pharmacologically active in inducing an erection. Other substances, such as water, buffers, salts, preservatives and the like, which are not pharmacologically active in inducing an erection, may be present in the composition.

As used herein, all volumes and volume-dependent concentrations recited herein are intended to be at 25° C.

Compositions

Composition that are effective to induce an erection in a human male, suffering from impotence of any origin, other than anatomical deficiencies that preclude an erection sufficient for vaginal penetration, are provided. In particular, these compositions may be used to induce an erection in a male suffering from impotence caused by severe atherosclerosis and also impotence that is neurogenic or psychogenic in origin. The composition is formulated in a carrier that is physiologically acceptable for administration to a human male by intracavernosal injection. The composition is formulated such that it has a pH of between about 2 and about 4.5, preferably between about 2 and about 3.5 and most preferably about 3 and contains: (i) VIP and/or PHM; and, in instances in which the impotence is not of psychogenic or neurogenic origin, (ii) an alpha-adrenergic blocker. The concentrations of erection inducing ingredients is effective to induce an erection in a male suffering from impotence sufficient for vaginal penetration.

VIP is human vasoactive intestinal peptide, a known, 28-amino acid, carboxy-terminal aminated neuropeptide (see, e.g., Ottesen et al (1983) *Eur. J. Clin. Invest.* 13:321–324; U.S. Pat. Nos. 4,757,133; and 3,898,329). "PHM" is peptide N-terminal histidine C-terminal methionineamide, a known, 27-amino acid, carboxy-terminal aminated, human neuropeptide (see, e.g., Itoh et al. (1983) *Nature* 304:547–549; and Bodner et al. (1985) *Proc. Nat'l. Acad. Sci. USA* 8.2:3548–3551). Reference to a mass of VIP or PHM in a composition is to the mass of the polypeptide rather than that of the acid addition salt of the polypeptide, in case the composition were prepared with such a salt of the polypeptide.

Numerous compounds are known in the pharmacological arts to be alpha-adrenergic blockers and all of these compounds are comprehended by the term "alpha-adrenergic blocker" as used in the present specification (see, e.g., Weiner, (1980) "Drugs that Inhibit Adrenergic Nerves and Block Adrenergic Receptors," in Goodman and Gilman, eds., The Pharmacological Basis of Therapeutics", MacMillan Publishing Co., New York, N.Y., USA, 6th Ed., p. 179). Alpha-adrenergic blockers include, among others, phentolamine and prazosin. Phentolamine chloride, phentolamine mesylate, and prazosin chloride are preferred forms of phentolamine and prazosin for use herein. Unless otherwise noted, reference to a mass of an alpha-adrenergic blocker in a composition is to the mass that the blocker would have in the composition if all of the blocker were present as the chloride salt.

Physiologically acceptable compositions are aqueous solutions that are physiologically acceptable for administration by intracavernosal injection into the penis. The physiologically acceptable carrier is selected such that it is not painful or irritating upon intracavernosal injection. The physiological composition for use herein has a pH of between about 2 and about 4.5, preferably between about 2 and about 3.5 and most preferably about 3. Thus, in addition to water, VIP or PHM (or both) and, possibly also, alpha-adrenergic blocker(s), such a composition includes physiologically acceptable buffers, salts, preservatives and the like at physiologically acceptable concentrations at the requisite pH. The physiologically acceptable compositions, will preferably be sterile at the time of administration by intracavernosal injection.

Among the physiologically acceptable compositions for use in the methods is physiological saline or phosphate buffered saline, in which VIP or PHM or both (optionally in the form of non-toxic salt(s)) and possibly also an alpha-adrenergic blocker (also optionally in the form of a non-toxic salt) are dissolved or suspended, such that the resulting composition is suitable for intracavernosal injection. Such a physiologically acceptable composition can also include a non-irritant preservative, such as, e.g., benzalkonium chloride at 0.05% (w/v) to 0./2% (w/v). As the skilled artisan will understand, there are numerous non-toxic salts of VIP, PHM and alpha-adrenergic blockers that can be employed in a physiologically acceptable composition for use in the methods herein, including, among others, the chloride, bromide, acetate, sulfate, and mesylate salts.

The salts and buffers are selected such the pH of the resulting solution is buffered between about 2 and about 4.5 and is preferably between 2 and 3.5 and most preferably about 3. Phosphate buffered saline is the preferred buffer. The concentration should be sufficient to maintain the pH and is generally around 10 mM. Any buffer that is suitable for use at this pH range may be used, as long as it does not cause pain or irritation upon intracavernosal injection.

Methods of preparing compositions for use will be readily apparent to the skilled artisan. Thus, the sterile, pharmacologically active substances (VIP, PHM and alpha-adrenergic blocker) are dissolved or mixed to the desired concentration in the sterile aqueous buffer, which contains the other substances of the composition. The peptide or peptides, and the alpha-adrenergic blocker, if any, of a composition can be combined with the aqueous solution to make the composition immediately prior to administration thereof or at any desirable time prior to administration thereof. By selection of the pH in the range of about 2 to about 4.5 the compositions may be prepared up to several months and perhaps longer prior to use and stored at temperatures of 0° C. to about 20° C.

If a composition is prepared more than a few hours prior to the time it is used the composition will desirably include a preservative, such as a benzalkonium salt, cresol, or the like, as understood in the art, and will preferably be held at a temperature between about 0° C. and about 20° C. until use.

Desirably, a single dose of a composition employed in the methods herein has a volume between about 0.1 ml and about 5 ml, and preferably about 1 ml. Thus, the concentrations of peptide(s) and blocker (if any) in such a composition desirably are set to place the volume of a single dose, with the intended quantities of peptide(s) and blocker (if any) for the dose, within such range of about 0.1 ml to about 5 ml. As indicated above, an erection is induced by a single dose of a composition provided herein. For at least several hours after injection suitable sexual stimulation will result in an erection sufficient for vaginal penetration.

The dose of VIP or PHM, and alpha-adrenergic blocker (if any), most, most suitable to induce an erection sufficient for vaginal penetration in a male suffering from impotence will vary somewhat depending on the disfunction(s) underlying the impotence, the age, the general medical condition, and the condition of the cardiovascular system of the male, and whether the male is being treated with drugs, such as beta-blockers, that may impair erectile sufficiency. In any case, a skilled physician will be able to determine readily a suitable dose of VIP or PHM, and a suitable dose of an alpha-adrenergic blocker, if any, to be administered together with the VIP or PHM to induce an erection in a male in accord with the methods provided herein.

Compositions for treatment of impotence that is of psychogenic or neurogenic origin A dose of PHM in the range of between about 10-15 $\mu$g and about 45-50 $\mu$g, and most preferably about 30 $\mu$g, a dose of VIP in the range of 15 $\mu$g-20 $\mu$g and about 50-60 $\mu$g, and most preferably between about 20 $\mu$g-30 $\mu$g, or a mixture of VIP and PHM such that the total concentration is within the ranges set forth for VIP, is effective for inducing an erection in a male suffering from impotence, which is substantially only neurogenic or psychogenic. When coupled with sexual stimulation, virtually all males suffering from such impotence will achieve an erection sufficient for vaginal penetration with intracavernosal injection of a dose of 30 $\mu$g in a physiologically acceptable diluent, and many will achieve such an erection with a dose as low as 10 $\mu$g.

PHM has a somewhat longer lasting pharmacological effect than VIP at the same dosage. Thus, it can be expected that PHM can be used at a lower dosage than VIP to achieve the same effect as VIP and, consequently, that the magnitude of potential side-effects (hypotension, increased pulse rate, flushing of the face and trunk) that have been observed when higher doses (greater than about 40 $\mu$g) of VIP are used to induce an erection, can be reduced when PHM is used in place of VIP by using the PHM at a lower dosage.

A preferred composition to effect an erection in male suffering from impotence, which is substantially only neurogenic or psychogenic, in accord with the methods herein, is a solution of PHM or VIP at 30 $\mu$g/ml in phosphate buffered saline at pH between about 2 and about 4.5, preferably between about 2 and about 3.5 and most preferably about 3, with the PHM or VIP the only substance in the solution that is pharmacologically active in inducing an erection. Preferably 1 ml of the preferred composition is administered as a bolus by injection into a corpus cavernosum while the penis is constricted at its base with a tourniquet. About 5-10 minutes after the injection, the tourniquet is released and, if not already started before the tourniquet is released, sexual stimulation is begun. An erection sufficient for vaginal penetration is then achieved typically within 5 minutes. Priapism does not occur. The composition, however, the time between administration and sexual stimulation may be longer, if necessary.

Compositions for treatment of impotence that is of any origin that is pharmacologically treatable, particularly impotence that is caused by severe atherosclerosis VIP, PHM or mixtures of VIP and PHM are not effective in inducing erections in males suffering from impotence whose origin is severe atherosclerosis. Compositions for inducing erections in males suffering from impotence caused by severe atherosclerosis or any pharmacologically treatable cause include an a-adrenergic blocker and VIP and/or PHM.

Coupled with sexual stimulation, administration by intracavernosal injection of one of the neuropeptides (or a mixture of both) with an alpha-adrenergic blocking agent is effective to induce an erections sufficient for vaginal penetration in a male suffering from impotence, of any origin other than impotence that is untreatable by pharmacological means.

In the compositions for use in the methods of inducing an erection in a male suffering form impotence, including that in which severe atherosclerosis is a cause, VIP and PHM will be present at a concentration such that, upon the intracavernosal injection of a predetermined volume of the composition to induce an erection, between about 20 $\mu$g and about 100 $\mu$g, and more preferably between about 20 $\mu$g and about 70 $\mu$g, of neuropeptide will be administered. To minimize side-effects when VIP is employed in such a composition, it is preferred that less than about 60 $\mu$g of VIP be administered. In most cases, it is found that 30 $\mu$g of VIP or PHM (together with alpha-adrenergic blocker) is sufficient to induce an erection sufficient for vaginal penetration in a male suffering from impotence. Thus, typical compositions of which 1 ml would be administered by intracavernosal injection to induce an erection in a male suffering from impotence contain between about 10 $\mu$g/ml and about 100 $\mu$g/ml, and more preferably about 30 $\mu$g/mo, of VIP or PHM (or VIP and PHM) with alpha-adrenergic blocker in phosphate buffered saline at a pH of between about 2 and about 4.5, preferably between about 2 and about 3.5, and most preferably about 3.

For inducing erections in males suffering from pharmacologically treatable impotence, including impotence caused by severe atherosclerosis, the concentration of alpha-adrenergic blocker in such a composition depends on the severity of the atherosclerosis, the potency of the blocker, the cause of the impotence and on the volume of composition that is to be administered to induce an erection. When phentolamine is the $\alpha$-adrenergic blocker, the concentration should be adjusted such that it is between about 50 $\mu$g and 5000 $\mu$g (and preferably about 2000 $\mu$g) is administered. When prazosin is used, the concentration should be adjusted such that between about 5 $\mu$g and about 1500 $\mu$g (and typically about 100 $\mu$g) is administered. The skilled artisan will readily understand, from the relative potencies of alphaadrenergic blockers in reducing hypertension, the doses of phentolamine and prazosin required, if the two are used in combination in a composition, and the dose of any other alpha-adrenergic blocker (alone or in combination with others) required to induce an erection in a male suffering from impotence, of which severe atherosclerosis is a cause. Of course, from the known doses, the concentrations of each ingredient in the compositions can be readily determined. As discussed above, impotence that is of psychogenic or neurogenic origin can be treated with compositions that contain PHM or VIP as the only erection-inducing ingredient. Also, the neuropeptide and a-adrenergic blocker may be administered in a single composition or may be administered sequentially. It is preferred that they be administered as a single composition that is prepared and sold as part of a kit that contains an injector (see, copending U.S. application Ser. Nos. 07/956,952 and 07/641,752 to Wacks). Such kits contain the compositions formulated at a pH of between about 2 and about 4.5, preferably between about 2 and 3.5, and most preferably about 3 for single dosage administration. The compositions are packaged or included in the kits in glass and plastic, such as, polyethylene, polypropylene and polycarbonate, bottles, vials or ampules or any suitable container customarily used to store compositions at temperatures between about 0° C. and about 20° C.

In preferred embodiments, three combinations of VIP with phentolamine have been found to be effective in inducing erections in males suffering from impotence of which severe atherosclerosis is a cause: 30 $\mu$g VIP with 500 $\mu$g phentolamine, 30 $\mu$g VIP with 1000 $\mu$g phentolamine, and 30 $\mu$g VIP with 3000 $\mu$g phentolamine.

It is contemplated that the composition will be obtained and used under the guidance of a physician.

Methods of treatment

Methods of inducing erections, sufficient for vaginal penetration, in males suffering from impotence of any substantially any origin except instances in which the deficiency is anatomical in nature and precludes an erection sufficient for vaginal penetration, are provided.

In certain embodiments, methods are provided for inducing erections in males suffering from impotence that is substantially only neurogenic or psychogenic in origin. These methods involve administering to the male by intracavernosal injection a physiologically acceptable composition that contains an erection-inducing-effective amount of PHM and/or VIP, and (B) sexually stimulating the male. The composition is formulated so that the pH is between about 2 and about 4.5, preferably between about 2 and 3.5, most preferably about 3.

In other embodiments, methods are provided for inducing an erections in a human male suffering from impotence of substantially any origin, other than origins that preclude an erection sufficient for vaginal penetration. These methods involve (A) administering to the male by intracavernosal injection a physiologically acceptable composition that contains and erection-inducing amount of (i) VIP and/or PHM and (ii) an alpha-adrenergic blocker; and (B) sexually stimulation the male. The composition is formulated so that the pH is between about 2 and about 4.5, preferably between about 2 and 3.5, most preferably about 3. These methods are particularly suitable for treating impotence caused by severe atherosclerosis. Impotence that is neurogenic or psychogenic in origin may also be treated by these methods.

In inducing an erection in a male suffering from impotence, including that in which severe atherosclerosis is a cause, essentially the same steps are followed as with using, PHM or VIP to induce an erection in a male suffering from impotence that is substantially only neurogenic or psychogenic. Thus, between about 0. 1 ml and about 5 ml, and preferably about 1 ml, of a physiologically acceptable composition containing one of VIP or PHM or a mixture thereof of and an alphaadrenergic blocker is administered as a bolus by intracavernosal injection during, or prior to the initiation of, sexual stimulation and preferably with the penis constricted at its base for between about 1 minute and about 15 minutes (preferably about 5 minutes–about 10 minutes) after the injection. If necessary, the time between injection and sexual stimulation may be longer, up to several hours.

Sexual stimulation as prescribed by these methods, includes any form of sexual stimulation that would induce an erection in a normal male who is not suffering from erectile insufficiency. The sexual stimulation can be that which occurs in the course of sexual relations between the male, whose erection is to be induced in accord with the methods provided herein, and another person or can be outside sexual relations with another person. Examples of methods of sexual stimulation include, alone or in combination, touching or erotically manipulating erogenous areas of the genital organs or other erogenous parts of the body; providing visual stimulation, as with a pornographic film or other form of sexually stimulative show or display; or providing vibratory stimulation to the penis, at between about 30 Hz and about 100 Hz with an amplitude of about 1 mm to about 5 ram, as can be provided, for example, by resting the penis on the table of a vibrating apparatus such as that of a Vibrector system (Multicept, Genofte, Denmark). In inducing an erection in an impotent male outside of sexual relations, as, for example, when a physician induces an erection in a patient suffering from psychogenic impotence, a preferred method of sexual stimulation includes providing visual stimulation, as with a pornographic film, simultaneously with vibratory stimulation of the penis, as with a Vibrector system set to between about 30 Hz and about 60 Hz (usually about 50 Hz)in frequency and between about 1 mm and about 2.5 mm (usually about 2.2 mm) in amplitude.

The sexual stimulation can begin before or after the intracavernosal injection. If the stimulation begins after the injection, it is preferably begun within 5 to 10 minutes to insure that there is significant overlap of the pharmacological effects of the neuropeptide(s) and alpha-adrenergic blocker(s), if any, in the composition administered by the injection and the stimulative effects of the sexual stimulation. Whether the stimulation begins before or after the injection, it will continue preferably at least until an erection sufficient for vaginal penetration is achieved.

In carrying out the methods, it is preferred that, for a period of time between about 1 minute and about 15 minutes (preferably about 5 minutes–10 minutes), the penis is constricted near the base thereof and between the base and the point at which the injection into a corpus cavernosum occurs, in order to limit loss of injected fluid from the corpus cavernosum before the ingredients in the fluid, that are active in inducing erection, have been able to have erection-inducing effects. The constriction can be effected by any means known in the art, such as with a tourniquet, cuff, rubber band or the like, or even manually, in order to slow the release of the injected fluid and the pharmacologically active substance(s) therein into the general circulation.

In practicing the methods, a single dose, with active ingredients in sufficient quantity to induce an erection, is administered as a bolus into the cavernous body. Preferably a thin (e.g., 26-gauge to 28-gauge) and short (10 mm to 13 mm) hypodermic needle is employed.

Typically, a 12 mm, 27-gauge needle is employed. In preferred embodiments, the composition is injected using the injector described in copending U.S. application Ser. Nos. 07/956,952 and 07/641,752 to Wacks.

Diagnosis of the origin or cause of impotence in a male

Diagnosis of impotence that is substantially only neurogenic or psychogenic in origin Determination whether a human male is suffering from impotence that is substantially only neurogenic or psychogenic is readily made by a person skilled in the art using a number of readily available diagnostic procedures. Thus, a male suffering from impotence can first be given a physical examination with particular attention to possible penile and scrotal pathology, whereby any anatomical deficiency precluding an erection sufficient for vaginal penetration can be detected, and then, in the absence of such an anatomical deficiency, can be subjected to tests, whereby penile venous leakage or severe or untreatable atherosclerosis can be detected.

Such tests include determination of the penobrachial blood pressure index (PBPI), doppler investigation of the penile arteries, and a papaverine test. The PBPI is the penile systolic blood pressure divided by the systolic blood pressure determined at one of the arms. These blood pressures can be determined by any numerous standard techniques. Thus, the penile systolic blood pressure can be determined by placing around the base of the free part of the penis in the flaccid state, an inflatable cuff, which is capable of being used to apply variable pressure, readable from a gauge, to an object around which the cuff is placed, localizing the penile arteries with a Doppler ultrasound probe (e.g., and 8 MHz probe, such as the Mini Doplex D500 ™ available from Huntleigh Technology, Luton, United Kingdom), and then inflating and deflating the cuff and ascertaining the pressure at which the Doppler sound reappears. The pressure at which the Doppler sound reappears is the penile systolic blood pressure. A male's penile blood pressure is regarded as normal if his PBPI is >0.80.

With regard to Doppler investigation, each of the two penile cavernous arteries is investigated distal to the aforementioned cuff using the Doppler ultrasound problem. The function of each of the two arteries is assessed by Doppler ultrasound using an arbitrary scale of 0, 1, 2 or 3, where 0 means that the function is so deficient that the artery cannot be located and 3 means that the artery is well enough that maximal Doppler sound is observed.

In the papaverine test, a tourniquet is placed at the base of the free part of the penis and tightened and then, with the patient seated, 30 mg of papaverine in 1 ml of a physiologically acceptable fluid such as physiological saline or phosphate-buffered saline is injected into the penile cavernous body. (In persons suspected of having impotence due to a suprasacral nerve lesion or a psychogenic dysfunction, only 15 mg of papaverine is administered, because of the high incidence of papaverine-induced priapism in such cases.) Five minutes after the injection, the tourniquet is removed and an ultrasound Doppler investigation of the penile cavernous arteries is carried out as described above. The function of the arteries is regarded as normal if both of them score a 3 on the arbitrary scale. After the Doppler investigation, penile vibration, at about a 4 Hz with an amplitude of about 1.2 mm (carried out with, e.g., a Vibrector ™, from Multicept, Gentofte, Denmark) is carried out for five to ten minutes and then erectile response is evaluated. Erectile response is classified as full rigidity, if the angle between the penis and the legs in the standing position is >900°, and tumescence or no response if the angle is less than or equal to 45°. The papaverine employed in the "papaverine test" described above could be replace with VIP (approximately 50 $\mu$g).

An impotent male, who does not have an anatomical deficiency that would preclude having an erection sufficient for vaginal penetration, who has a PBPI >0.80, who has scores of 2 or 3 in Doppler ultrasound investigations of both of the cavernous arteries of the penis, after papaverine injection as described above, and who has a fully rigid erection after papaverine injection and vibration as described above, is suffering from impotence that, as used herein, is "substantially only neurogenic or psychogenic" in origin, as that phrase is employed in the present specification. It is possible that atherosclerosis or venous leakage contributes to such impotence, and atherosclerosis likely does contribute, if the score is less than 3 in the Doppler investigation of one or both of the cavernous arteries after papaverine injection; but any venous leakage or atherosclerosis in such impotence is not untreatable and, consequently, is not a "substantial" factor in the impotence and such atherosclerosis, if any, is less than "severe"(as the term "severe atherosclerosis" is employed herein).

Impotence, which is a side-effect of drugs, such as beta-blockers, is deemed to be neurogenic impotence in the present specification. Similarly, impotence which is a result of alcoholism or excessive consumption of alcohol, is deemed to be neurogenic or psychogenic impotence, for purposes of the present specification. Thus, a male who is diagnosed in accordance with the present specification as suffering from impotence that is "substantially only neurogenic or psychogenic" in origin is suffering from impotence that is substantially only neurogenic, psychogenic or neurogenic and psychogenic in origin, even though an underlying cause of the impotence has been identified as a side-effect of a drug, alcoholism or excessive consumption of alcohol.

Diagnosis of impotence that is untreatable by pharmacological means

Generally, a male with a PBPI less than about 0.60, with scores of 0 in Doppler investigations of both penile cavernous arteries (after papaverine injection as described above), and with a less than fully rigid erection after papaverine injection and vibration will have impotence caused by "untreatable" atherosclerosis.

Methods are available to ascertain whether impotence is untreatable because of venous leakage. One method of ascertaining whether untreatable venous leakage is a cause of impotence is by cavernosometry, optionally supplemented with cavernosography. See, e.g., Delcour et al. (1986) *Radiology* 161:799; Porst et al. (1987) *J. Urol.* 137:1163; Lue et al. (1987) *J. Urol.* 37:829). Cavernosometry can be done using, both before and after intracavernosal injection of 60 mg of papaverine (in 1 ml of physiological saline), infusion of physiological saline through a 19-gauge needle into one corpus cavernosum with a 21-gauge needle inserted into the other corpus cavernosum for measurement of intracorporal pressure (which is recorded on a plotter). The infusion rates needed to induce and maintain an erection are measure. If the infusion rate needed to maintain an erection is greater than 50 ml/min before administration of the papaverine and greater than 15 ml/min after administration of the papaverine, untreatable venous leakage is present. As long as an erection can be achieved at some flow rate less than about 100 ml/min before injection of the papaverine and less than about 50 ml/min after the injection of papaverine, it might be possible, using cavernosography, to locate the venous lesion associated with the leakage, and thereby confirm the diagnosis based on cavernosometry and provide information for possible surgical correction for the leakage. In the cavernosography, the penis is X-rayed, both before and after intracavernosal injection of 60 mg papaverine (in 1 ml of physiological saline), while infusing contrast medium into the corpus cavernosum (e.g., through a 19-gauge needle) at a flow rate that maintains an erection during the x-raying. Numerous contrast media suitable for the procedure are available in the art; these are typically aqueous solutions of iodinated compounds that provide between about 180 mg/ml and about 360 mg/ml of iodine. Examples are Omnipaque 240 TM, which is a solution of iohexol providing 240 mg/ml of iodine sold by Winthrop Pharmaceuticals, New York, N.Y., USA, and Iopamiro®, which is a solution of iopamidol providing 300 mg/ml iodine sold by Astra Meditec, Goteborg, Sweden. Typically 50–100 ml of the contrast medium will be employed for each x-ray (i.e., before and then after the injection of papaverine). In the cavernosometry and cavernosography, 30 mg papaverine (in 1 ml physiological saline) coupled with stimulation by vibration can be employed in place of 60 mg papaverine (in 1 ml physiological saline).

The following examples are included for illustrative purposes only and are not intended to limit the scope of the invention.

EXAMPLE 1

PREPARATION OF AMPULES CONTAINING VIP AND PHENTOLAMINE

Compositions containing VIP and phentolamine formulated for packaging in a kit or otherwise for storage have been prepared as follows:

| Composition per ml | Dosage/ml |
|---|---|
| COMPOSITION 1 | |
| VIP | 33.0 μg |
| Phentolamine mesylate | 1.1 mg |
| NaH$_2$PO$_4$ | 0.53 mg |
| H$_3$PO$_4$ | 0.06 mg |
| NaCl | 9.00 mg |
| COMPOSITION 2 | |
| VIP | 33.0 μg |
| Phentolamine mesylate | 2.20 mg |
| NaH$_2$PO$_4$ | 0.53 mg |
| H$_3$PO$_4$ | 0.06 mg |
| NaCl | 9.00 mg |

1. Preparation of 1 L, 1.00M sodium hydroxide (NaOH) solution.

In a suitably sized, clean borosilicate glass vessel, 40.0 grams sodium hydroxide (NaOH) pellets are dissolved in 900 mls sterile water that is suitable for injection with stirring. Sterile water suitable for injection is added to resulting mixture up to make the volume 1 L.

2. Preparation of 10 L 5 mM phosphoric acid/sodium dihydrogen phosphate, 0.9% NaCl, pH 3.00 (solution A).

In a suitably sized, clean, borosilicate glass vessel, 90 grams sodium chloride (NaCl) are dissolved in 900 mls sterile water that is suitable for injection with stirring. Then, 3.4 mls 85% ortho-phosphoric acid (H$_3$PO$_4$, 1711 g/L, 14.84M) and 36 mls 1.00 M NaOH solution (prepared in 1 above) are added and stirred for 1 min. The pH is adjusted with the 1.00M sodium hydroxide (NaOH) solution to 2.9–3.1. The resulting mixture is made up to 10 L by adding sterile water suitable for injection.

The mixture is degassed by rapid bubbling with argon using the recommended sparge head (Jones Chromatographic cat #6500-½, series 6500 solvent filter, stainless steel Type 316, pore size 2 μm or equivalent), at >400 mls/min for 10 minutes. A sample of the argon purged solution A is withdrawn and analyzed for oxygen content using CHEMetrics dissolved oxygen test kit (Model 0-1), cat K-7501, according to the instructions of the manufacturer. All precautions should be taken to ensure that the test sample of the solution does not come into contact with air. If the dissolved oxygen level is greater than 0.85±0.1 ppm, argon purging is resumed until the measured level is reduced to 0.85±0.1 ppm. The final oxygen content is noted.

3. Addition of phentolamine and VIP

The following procedures require the use of a clean stainless steel vessel fitted with a stirring system and an inlet for argon flow. VIP (330 mg) and phentolamine mesylate (phentolamine methane sulfonate) (11 g for composition 1 or 22 g for composition 2) are weighed out and placed in the stainless steel, argon filled vessel. While maintaining a flow or argon, solution A is added to 10 L with and stirred until the VIP and phentolamine are fully dissolved. A 1 ml sample is withdrawn and the pH is checked and noted. The sample is discarded.

4. Sterile filtration

The solution from step 3, should be sterilized by filtration through a 0.22 micron filter (Sartorius Minisart 0.22 micron filter or similar suitable filter) If necessary, the filtration can be performed under pressure of sterile argon.

5. Filling of ampules

Amber borosilicate ampules (2 ml) are filled with 1 ml (1.16 ml) of the solution from 4, using sterile techniques. The ampules are then filled with argon prior to sealing. Filled ampules are stored at 4° C.

6. Sterility Control

The sterility of the final product can be confirmed according to the criteria described in Ph. Eur 2nd Ed., §V.2.1. "Biological Safety Tests"§V2.1.1. "Sterility" or additional criteria as required by the jurisdiction in which the product will be distributed.

7. Pyrogenicity Control

The absence of pyrogens in the final product can be confirmed according to "Test for pyrogens" Ph. Eur, 2nd Ed., V.2.1.4.

Since modifications will be apparent to those of skill in this art, it is intended that this invention be limited only by the scope of the appended claims.

What is claimed is:

1. A composition formulated for single dosage administration to a human male by intracavernosal injection, comprising in a physiologically acceptable carrier:
   (i) a neuropeptide selected from the group consisting of vasoactive intestinal peptide (VIP) and peptide histidine methionine (PHM) and
   (ii) an alpha-adrenergic blocker, wherein:
   the amounts of the neuropeptide and blocker are, with sexual stimulation, effective, in the absence of other erection-inducing substances to induce an erection when administered together by intracavernosal injection to a human male suffering from impotence:
administration of a single dose of the composition does not cause priapism in a male treated therewith;
the induced erection is sufficient for vaginal penetration; and
the pH of the composition is between about 2 and about 4.5.

2. The composition of claim 1, wherein the amount of the neuropeptide is between 15 µg and 60 µg.

3. The composition of claim 2, wherein the neuropeptide is VIP.

4. A composition of claim 2, wherein the neuropeptide is PHM.

5. The composition of claim 2, wherein the alpha-adrenergic blocker is selected from the group consisting of phentolamine, at a concentration of between 20 µg/ml and 20 mg/ml, and prazosin, at a concentration of between 2 µg/ml and 10 mg/ml.

6. The composition of claim 3, wherein the alpha-adrenergic blocker is selected from the group consisting of phentolamine, at a concentration of between 20 µg/ml and 20 mg/ml, and prazosin, at a concentration of between 2 µg/ml and 10 mg/ml.

7. The composition of claim 1, wherein the physiologically acceptable carrier is phosphate buffered saline at about pH 3.0.

8. A composition that is physiologically acceptable for administration to a human male by intracavernosal injection, consisting essentially of:
(a) 5–500 µg/ml of vasoactive intestinal peptide (VIP) peptide or histidine methionine (PHM); and
(b) 20 µg/ml–20 mg/ml of phentolamine in a physiologically acceptable solution,
wherein the pH of the composition is between about 2 and about 4.5.

9. The composition of claim 8, wherein the physiologically acceptable solution is phosphate buffered saline at a pH about 3.0.

10. The composition of claim 8, wherein the concentration of VIP or PHM is about 15 µg/ml to 60 µg/ml, the composition of phentolamine is between about 1 and 2 mg/ml.

11. A method of inducing an erection in a human male suffering from impotence, comprising:
(A) administering to the male by intracavernosal injection an erection-inducing-effective amount of peptide histidine methionine (PHM) or vasoactive intestinal peptide (VIP) in a physiologically acceptable solution; and
(B) sexually stimulating the male, wherein:
the amount of PHM or VIP is effective in the absence of any other erection-inducing compounds to induce an erection sufficient for vaginal penetration in the presence of sexual stimulation in the male;
the impotence is substantially neurogenic or psychogenic impotence; and the pH of the composition is between about 2 and about 4.5.

12. The method of claim 11, wherein the volume of the physiologically acceptable solution administered to the male is between 0.1 ml and 5 ml, the amount of VIP administered is between about 15 µg and 60 µg and the amount of PHM administered is between 10 µg and 60 µg.

13. A method of inducing an erection sufficient for vaginal penetration in a human male suffering from impotence, comprising:
(A) administering the composition of claim 1 to the male by intracavernosal injection; and
(B) sexually stimulating the male.

14. The method of claim 13, wherein the neuropeptide is VIP.

15. The method of claim 13, wherein the neuropeptide is PHM.

16. The method of claim 14, wherein the volume of the injected, physiologically acceptable composition is between 0.1 ml and 5 ml, and the alpha-adrenergic blocker is selected from the group consisting of phentolamine, at a dose between 0.1 mg and 5 mg and prazosin, at a dose between 0.01 mg and 1 mg.

17. The method of claim 14, wherein the alpha-adrenergic blocker is phentolamine.

18. The method of claim 14, wherein the pH of the composition is about 3.

19. A composition formulated for single dosage administration to a human male by intracavernosal injection, comprising in a physiologically acceptable carrier:
(i) a neuropeptide selected from the group consisting of vasoactive intestinal peptide (VIP) and peptide histidine methionine (PHM), wherein:
the amount of the neuropeptide is, with sexual stimulation, effective, in the absence of other erection-inducing substances to induce an erection when administered intracavernosal injection to a human male suffering from impotence that is substantially of neurogenic or psychogenic origin;
administration of a single dose of the composition does not cause priapism in a male treated therewith;
the induced erection is sufficient for vaginal penetration; and
the pH of the composition is between about 2 and about 4.5.

20. The composition of claim 19, wherein the pH is about 3.

21. A kit, comprising a container containing the composition of claim 1 formulated for single dosage administration.

22. A kit, comprising a container containing the composition of claim 8 formulated for single dosage administration.

23. A kit, comprising a container containing the composition of claim 19 formulated for single dosage administration.

* * * * *

UNITED STATES PATENT AND TRADEMARK OFFICE
CERTIFICATE OF CORRECTION

PATENT NO. : 5,447,912
DATED : September 5, 1995
INVENTOR(S) : Thomas Gerstenberg et al.

It is certified that error appears in the above-indentified patent and that said Letters Patent is hereby corrected as shown below:

Column 15, line 35, change "peptide or" to --or peptide--.

Signed and Sealed this

Ninth Day of July, 1996

Attest:

BRUCE LEHMAN

Attesting Officer

Commissioner of Patents and Trademarks